United States Patent [19]

Pehu et al.

[11] Patent Number: 5,968,828
[45] Date of Patent: *Oct. 19, 1999

[54] VIRUS-RESISTANT TRANSGENIC PLANTS COMPRISING CELLS TRANSFORMED WITH A POLYNUCLEOTIDE ENCODING A POTYVIRIDAE P1 PROTEIN OR P1 PROTEIN FRAGMENT

[75] Inventors: Eija Pehu, Helsinki, Finland; Tuula Pehu, College Station, Tex.; Tuula Maki-Valkama, Helsinki, Finland; Jari Valkonen, Helsinki, Finland; Kimmo Koivu, Helsinki, Finland; Kirsi Lehto, Kaarina, Finland

[73] Assignee: Helsinki University Licensing Ltd. Oy, Helsinki, Finland

[*] Notice: This patent is subject to a terminal disclaimer.

[21] Appl. No.: 08/751,233

[22] Filed: Nov. 18, 1996

Related U.S. Application Data

[63] Continuation-in-part of application No. 08/246,123, May 19, 1994, Pat. No. 5,576,202.
[51] Int. Cl.⁶ .............................. C12N 15/00; C12N 5/14; A01H 1/04; C07H 21/04
[52] U.S. Cl. ........................ 435/418; 435/419; 435/425; 435/429; 800/279; 800/280; 800/286; 800/287; 800/288; 800/FOR 102; 800/FOR 107; 536/23.2; 536/23.72; 536/24.1
[58] Field of Search .................................... 800/279, 280, 800/286, 287, 288, FOR 102, FOR 107; 435/419, 418, 425, 429; 536/23.72, 23.2, 24.1

[56] References Cited

U.S. PATENT DOCUMENTS

| | | | |
|---|---|---|---|
| 5,576,202 | 11/1996 | Pehu et al. | 435/172.3 |
| 5,589,612 | 12/1996 | Jilka et al. | 800/205 |

FOREIGN PATENT DOCUMENTS

| | | | |
|---|---|---|---|
| 0 578 627 A1 | 1/1994 | European Pat. Off. | C12N 15/82 |
| WO 89/12100 | 12/1989 | WIPO . | |
| WO 94/16087 | 7/1994 | WIPO | C12N 15/82 |

OTHER PUBLICATIONS

Donson et al., "Broad Resistance to Tobamoviruses Is Mediated by a Modified Tobacco Mosaic Virus Replicase Transgene," *Molecular Plant–Microbe Interact.*, 6(5):635–642 (1992).
Anderson et al., "A defective replicase gene induces resistance to cucumber mosaic virus in transgenic tobacco plants," *Proc. Nat'l. Acad. Sci., USA*, 89:8759–8763 (Sep., 1992).
Audy et al., "Replicase–Mediated Resistance to Potato Virus Y," *American Society for Virology, 12th Annual Meeting*, University of California at Davis, California, p. A54, Jul. 10–14, 1993 (Abstract 24–1).
Audy et al., "Replicase–Mediated Resistance To Potato Virus Y In Transgenic Tobacco Plants," *Mol. Plant–Microbe Interac.*, 7(1):15–22 (1994).
Ausubel et al., (Ed.), "The Polymerase Chain Reaction," *Current Protocols in Molecular Biology*, Section 15 (1989).
Barnett et al., "Potyviridae, a proposed family of plant viruses," *Arch. Virology*, 118:139–141 (1991).
Brantley and Hunt, "The N–terminal protein of the polyprotein encoded by the potyvirus tobacco vein mottling virus is an RNA–binding protein," *J. Gen. Virol.*, 74:1157–1162 (1993).
Dougherty et al., "Expression of Virus–Encoded Proteinases: Functional and Structural Similarities With Cellular Enzymes," *Microbiological Reviews*, pp. 798–801 (Dec., 1993).
Guo et al., "Delayed Resistance to Plum Pox Potyvirus Dediated by a Mutated RNA Replicase Gene: Involvement of a Gene–Silencing Mechanism," *Molecular Plant–Microbe Interact.*, 10:160–170 (1997).
Lomonosoff, "Pathogen–Derived Resistance to Plant Viruses," *Annu. Rev. Phytopathol*, 33:323–343 (1995).
MacFarlane et al., "Plants Transformed With a Region of the 201 Kilodalton Replicase Gene From Pea Early Browning Virus RNA1 are Resistant to Virus Infection," *Proc. Nat'l. Acad. Sci, USA*, 89:5829–5833 (Jul., 1992).
Rubino et al., "Characterization of Resistance to Cymbidium Ringspot Virus in Transgenic Plants Expressing a Full–Length Viral Replicase Gene," *Virology*, 212:240–243 (1995).
Shukla et al., *The Potyviridae*, United Kingdom, University Press, Cambridge, (1994), pp. 92–99.
Tenllado et al., Resistance to Pepper Mild Mottle Tobamovirus Conferred by the 54–kDA Gene Sequence in Transgenic Plants Does Not Require Expression of the Wild–Type 54 kDa Protein, *Virology*, 219:333–335 (1996).
Thole et al., "Cloning and Sequencing of Potato Virus Y (Hungarian Isolate) Genomic RNA,"*Gene*, 123:149–156 (1993).
Verchot et al., "Debilitation of Plant Potyvirus Infectivity by P1 Proteinase–Inactiving Mutations and Restoration by Second–Site Modifications," *Journal of Virology*, 69(3):1582–1590 (Mar., 1995).
Verchot et al., "Evidence That the Potyvirus P1 Proteinase Functions in trans as an Accessory Factor for Genome Amplification," *Journal of Virology*, 69(6):3668–3674 (Jun., 1995).

(List continued on next page.)

*Primary Examiner*—Jeffrey Stucker
*Assistant Examiner*—Phuong T. Bui
*Attorney, Agent, or Firm*—Marshall, O'Toole, Gerstein, Murray & Borun

[57] ABSTRACT

Provided are transgenic plants with resistance to viral infection polynucleotides and methods for conferring such resistance, and methods for producing the transgenic plants. Plants transformed with a nucleotide sequence encoding a P1 protein of potato virus Y result in plants having increased resistance to infection by potato virus Y.

31 Claims, 2 Drawing Sheets

OTHER PUBLICATIONS

Braun and Hemenway, "Expression of Amino–Terminal Portions or Full–Length Viral Replicase Genes in Transgenic Plants Confers Resistance To Potato Virus X Infection," *Plant Cell,* 4:735–744 (Jun., 1992).

Cannon et al., "Organ–Specific Modulation of Gene Expression in Transgenic Plants Using Antisense RNA," *Plant Mol. Biol.,* 15:39–47 (1990).

Carr et al., "Resistance to Tobacco Mosaic Virus Induced by the 54–kDa Gene Sequence Requires Expression of the 54–kDa Protein," *Mol. Plant–Microbe Interac.,* 5(5):397–404 (1992).

Dellaporta et al., "A Plant DNA Minipreparation: Version II," *Plant Mol. Biol. Rep.,* 1(4):19–21 (1983).

Dougherty and Carrington, "Expression and Function of Potyviral Gene Products," *Ann. Rev. Phytopathol.,* 26:123–143 (1988).

Edwards et al., "A simple and rapid method for the preparation of plant genomic DNA for PCR analysis," *Nuc. Acids Res.,* 19(6):1349 (1991).

Elomaa et al., "Agrobacterium–Mediated Transfer of Antisense Chalcone Synthase cDNA to *Gerbera hybrida* Inhibits Flower Pigmentation," *Bio/Technology,* 11:508–511 (Apr., 1993).

GenBank Accession No. A08776, "Potato virus Y complete genome RNA," dated Nov. 27, 1993.

GenBank Accession No. D00424, "Plum pox virus, complete genome," deposited by Maiss et al., dated Nov. 27, 1992.

GenBank Accession No. D01152, "Pea seed–borne mosaic virus mRNA, complete cds.," deposited by Johansen et al., dated Aug. 6, 1993.

GenBank Accession No. D10927, "Turnip mosaic virus genomic RNA for Capsid protein, complete cds.," deposited by Nicolas et al., dated Jan. 13, 1993.

GenBank Accession No. D10930, "Pea seed–borne mosaic virus mRNA, complete cds.," deposited by Johansen et al., dated Aug. 6, 1993.

GenBank Accession No. D13751, "Plum pox virus, complete genome," deposited by Maiss et al., dated Nov. 27, 1992.

GenBank Accession No. D83749, "Bean yellow mosaic virus genomic RNA for polyprotein, complete cds." deposited by Nakamura et al., dated Dec. 2, 1996.

GenBank Accession No. L29569, "Zucchini yellow mosaic virus polyprotein; P1 protease; helper component–protease; P3 protein; cylindrical inclusion protein; P6K; VPg; NIa protease; NIb replicase, and capsid protein," deposited by Wisler et al., dated Apr. 28, 1995.

GenBank Accession No. L31350, "Zucchini yellow mosaic virus polyprotein, complete cds; P1 protease; P2 HC–protease; cylindrical inclusion protein; protease; replicase; capsid protein," deposited by Wisler et al., dated Apr. 28, 1995.

GenBank Accession No. L35588, "Zucchini yellow mosaic virus P1 protease, 5' end," deposited by Wisler et al., dated Apr. 28, 1995.

GenBank Accession No. L35589, "Zucchini yellow mosaic virus P1 protease, 5' end," deposited by Wisler et al., dated Apr. 28, 1995.

GenBank Accession No. L35590, "Zucchini yellow mosaic virus P1 protease, helper component, and P3 protease; 5' end," deposited by Wisler et al., dated Apr. 28, 1995.

GenBank Accession No. L38714, "Tobacco etch virus P1, helper component and proteinase, P3, cylindric inclusion, nuclear inclusion a, nuclear inclusion b, and coat protein gene, complete cds.," deposited by Chu et al., dated Apr. 30, 1996.

GenBank Accession No. M37180, "Potato virus Y helper component mRNA, 5' end," deposited by Thronbury et al., dated Aug. 6, 1990.

GenBank Accession No. M38480, "Potato virus X complete genome," deposited by Kraev et al., dated Mar. 13, 1992.

GenBank Accession No. M92280, "Plum pox potyvirus polyprotein gene, complete cds.," deposited by Palkovics et al., dated Aug. 8, 1996.

GenBank Accession No. M95491, "Potato virus Y polyprotein gene, complete cds.," deposited by Thole et al., dated Mar. 22, 1993.

GenBank Accession No. M96425, "Pepper mottle virus complete genome," deposited by Vance et al., dated Dec. 18, 1992.

GenBank Accession No. U05771, "Peanut stripe virus, complete genome," deposited by Cassidy et al., date May 30, 1996.

GenBank Accession No. U19287, "Bean common mosaic virus polyprotein gene, complete cds.," deposited by Fang et al., dated Jun. 12, 1996.

GenBank Accession No. U34972, "Peanut stripe virus mRNA polyprotein mRNA, complete cds.," deposited by Flasinski et al., dated Oct. 10, 1995.

GenBank Accession No. U38621, "Tobacco vein mottling virus VAM–resistance–breaking strain (TVMV–S), complete sequence," deposited by Nicolas et al., dated Nov. 9, 1995.

GenBank Accession No. U42596, "Yam mosaic virus genome, complete sequence," deposited by Aleman et al., dated Sep. 21, 1996.

GenBank Accession No. U47033, "Bean yellow mosaic potyvirus polyprotein mRNA, complete cds.," deposited by Guyatt et al., dated Dec. 3, 1996.

GenBank Accession No. X12456, "Potatovirus Y strain N genomic RNA," deposited by Robaglia, C., dated Jan. 18, 1994.

GenBank Accession No. X53062, "Potato virus M complete genome," deposited by Zavriev, S.K., dated Sep. 12, 1993.

GenBank Accession No. X55802, "Potato Virus X complete genomic RNA," deposited by Mentaberry, A.N., dated Apr. 21, 1992.

GenBank Accession No. X56759, "Plum pox potyvirus polyprotein gene, complete cds.," deposited by Palkovics et al., dated Aug. 8, 1996.

GenBank Accession No. X69757, "Barley yellow mosaic virus RNA for polyprotein RNA1," deposited by Peerenboom, E., dated Jan. 25, 1993.

GenBank Accession No. X81083, "Plum pox potyvirus complete genomic RNA," deposited by Maiss et al., dated Aug. 18, 1994.

GenBank Accession No. X82625, "Barley mild mosaic virus mRNA for RNA2 polyprotein," deposited by Dessens et al., dated Apr. 20, 1995.

GenBank Accession No. X82848, "Potato virus Y P1 gene," deposited by Pehu et al., dated May 20, 1995.

GenBank Accession No. X89997, "Pea seed–borne mosaic virus complete genome," deposited by Johansen et al., dated Jun. 25, 1996.

GenBank Accession No. X97895, "Potato virus Y genes encoding viral polyprotein," deposited by Jakab et al., dated Jul. 10, 1996.

GenBank Accession No. Z21670, "Potato virus A complete genome," deposited by Puurand et al., dated Feb. 13, 1995.

GenBank Accession No. Z48506, "Brome streak mosaic rymovirus polyprotein RNA," deposited by Gotz et al., dated Sep. 20, 1995.

Gibson et al., "Resistance to potato virus Y and potato virus X in *Solanum brevidens*," *Ann. Appl. Biol.*, 116:151–156 (1990).

Golemboski et al., "Plants transformed with a tobacco mosaic virus nonstructural gene sequence are resistant to the virus," *Proc. Nat'l Acad. Sci., USA*, 87:6311–6315 (Aug., 1990).

Herskowitz, I., "Functional inactivation of genes by dominant negative mutations," *Nature*, 329:219–222 (Sep. 17, 1987).

Horsch et al., "A Simple and General Method For Transferring Genes Into Plants," *Science*, 227:1229–1231 (Mar. 8, 1985).

Hull and Davies, "Approaches to Nonconventional Control of Plant Virus Diseases," *Crit. Rev. Plant. Sci.*, 11(1):17–33 (1992).

Kaniewski et al., "Field Resistance of Transgenic Russet Burbank Potato To Effects of Infection By Potato Virus X and Potato Virus Y," *Bio/Technology*, 8:750–754 (Aug., 1990).

Lawson et al., "Engineering Resistance to Mixed Virus Infection in a Commercial Potato Cultivar: Resistance to Potato Virus X and Potato Virus Y in Transgenic Russet Burbank," *Bio/Technology*, 8:127–134 (Feb., 1990).

Longstaff et al., "Extreme resistance to potato virus X infection in plants expressing a modified component of the putative viral replicase," *EMBO J.*, 12(2):379–386 (1993).

Maiti et al., "Plants that express a potyvirus proteinase gene are resistant to virus infection," *Proc. Nat'l. Acad. Sci., USA*, 90:6110–6114 (Jul., 1993).

Malyshenko et al., "Reduction of tobacco mosaic virus accumulation in transgenic plants producing non-functional viral transport proteins," *J. Gen. Virol.*, 74:1149–1156 (1993).

McDonnell et al., "A Simplified Method for the Detection of Neomycin Phosphotransferase II Activity in Transformed Plant Tissues," *Plant Mol. Biol. Rep.*, 9(4):380–386 (1987).

Murashige and Skoog, "A Revised Medium For Rapid Growth and BioAssays With Tobacco Tissue Cultures," *Physiologia Plantarum*, 15:473–497 (1962).

Pehu et al., "Potato Plants Transformed With Potato Virus Y P1 Gene Sequence Are Resistant to PVY$^{-O}$," *American Potato J.*, 72:523–532 (1995).

Reichmann et al., "Highlights and Prospects of Potyvirus Molecular Biology," *J. Gen. Virol.*, 73:1–16 (1992).

Robaglia et al., "Nucleotide Sequence of Potato Virus Y (N Strain) Genomic RNA," *J. Gen. Virol.*, 70:935–947 (1989).

Sambrook et al., In: *Molecular Cloning: A Laboratory Manual*, Sections 7.3–7.84 and 8.3–8.82 (1989).

Sanford and Johnston, "The Concept of Parasite–Derived Resistance–Deriving Resistance Genes from the Parasite's Own Genome," *J. Theor. Biol.*, 113:395–405 (1985).

Sanger et al., "DNA sequencing with chain–terminating inhibitors," *Proc. Nat'l. Acad. Sci., USA*, 74(12):5463–5467 (Dec., 1977).

Thornbury et al., "Comparative Sequence of the Helper Component (HC) Region of Potato Virus Y and a HC–Defective Strain, Potato Virus C," *Virology*, 178:573–578 (1990).

Van Haute et al., "Intergenetic transfer and exchange recombination of restriction fragments cloned in pBR322: a novel strategy for the reversed genetics of the Ti Plasmids of *Agrobaterium tumefaciens*," *EMBO J.*, 2(3):411–417 (1983).

Van Larebeke et al., "Large plasmid in *Agrobacterium tumefaciens* essential for the crown gall–inducing ability," *Nature*, 252:169–170 (Nov. 8, 1974).

Vardi et al., "Plants transformed with a cistron of a potato virus Y protease (NIa) are resistant to virus infection," *Proc. Nat'l. Acad. Sci., USA*, 90:7513–7517 (Aug., 1993).

Verchot et al., "The 35–kDa Protein from the N–Terminus of the Potyviral Polyprotein Functions as a Third Virus–Encoded Proteinase," *Virology*, 185:527–535 (1991).

Zambryski et al., "Ti plasmid vector for the introduction of DNA into plant cells without alteration of their normal regeneration capacity," *EMBO J.*, 2(12):2143–2150 (1983).

5,968,828

VIRUS-RESISTANT TRANSGENIC PLANTS COMPRISING CELLS TRANSFORMED WITH A POLYNUCLEOTIDE ENCODING A POTYVIRIDAE P1 PROTEIN OR P1 PROTEIN FRAGMENT

This application is a continuation-in-part of U.S. patent application Ser. No. 08/246,123, filed May 19, 1994, now U.S. Pat. No. 5,576,202.

FIELD OF THE INVENTION

The present invention generally relates to materials and methods for conferring resistance to viral infection in plants. More specifically, the invention relates to transgenic plants and methods of their preparation, wherein said plants are resistant to infection by viruses.

BACKGROUND OF THE INVENTION

Plant pathogens, including plant viruses, have a profound impact on agricultural production. Accordingly, the control and eradication of certain plant viruses is of economic importance.

One plant pathogen of economic interest is the potato virus Y. Potato virus Y infects and damages several plant species, including members of the Solanaceae family. In one member of that family, comprising species of potato, infection by potato virus Y may result in as high as an 80% reduction in crop yield. However, despite its name, potato virus Y is pathogenic in a variety of plant species, including non-potato species.

Potato virus Y is a member of the Potyviridae family of viruses, the largest known group (family) of plant viruses. This family, in turn, is comprised of a number of genera, including genius Potyvirus (named after its type member, potato virus Y), genus Baymovirus (type member: barley yellow mosaic virus), and genus Ryemovirus (type member: ryegrass mosaic virus). See generally, Barnett, O. W., *Archives of Virology*, 118:139–141 (1991); and Reichmnann et al., *J. General Virology*, 73:1–16 (1992). Significant research has been conducted relating to the genomic structure, organization, and expression of potyviruses. See, e.g., Reichmann et al. (1992). Genomic sequence information is now available for several members of the Potyviridae family. See, e.g., sequences reported in GenBank Accession Nos. M95491, A08776, D00441, X12456 and X97895 (potato virus Y); M38480 and X55802 (potato virus X); X53062 (potato virus M); Z21670 (potato virus A); U19287 (bean common mosaic virus); D83749 and U47033 (bean yellow mosaic virus); X81083, M92280, X56759, D13751 and D00424 (plum pox virus); M96425 (pepper motile virus); X89997, D10930 and D01152 (pea seed-borne mosaic virus); D10927 (turnip mosaic virus); L29569, L31350, and L35588–L35590 (zucchini yellow mosaic virus); X82625 (barley mild mosaic virus); X69757 (barley mosaic virus); Z48506 (brome streak mosaic rymovirus); U05771 and U34972 (peanut stripe virus) U42596 (yam mosaic virus); L38714 (tobacco etch virus); and U38621 (tobacco vein mottling virus), all incorporated by reference herein.

Of interest to the present invention is the P1 gene of viruses of the Potyviridae family, in particular the P1 gene of viruses of the potyvirus genus, especially of potato virus Y. The P1 gene sequence has been reported for a number of different virus species and strains, including those indicated in the preceding paragraph. The Pi gene encodes one of eight functional proteins produced by processing of a primary polyprotein encoded by the 9.7 Kb genome of potato virus Y. See Reichmann et al. (1992). Protein P1 is encoded near the 5' end of the viral genome and is a 35 kDa protein having C-terminal proteolytic activity. Id. The P1 protein also has been reported to bind RNA. Brantley, et al., *J. Gen. Virol.,* 74: 1157–1162 (1993).

Genetically-engineered pathogen-derived resistance to viral pathogens has been achieved in several plant species. For example, resistance to viral infection has been reported in plants transformed with viral coat protein-encoding genes. Hull, et al., *Crit. Rev. Plant Sci.,* 11: 17–33 (1992). Recently, there have been several reports that resistance to a plant virus may be achieved by transforming a susceptible plant with non-structural genes of the virus. However, such attempts have produced relatively strain-specific resistance. For example, strain-specific viral resistance has been reported by transformation of a strain of tobacco with replicase genes of tobacco mosaic virus. Longstaff, et al., *EMBO J.,* 12: 379–386 (1993). Similar strain-specific results in tobacco have been reported by transformation with potato virus Y. Audy, et al., 12 *Annual Meeting of the American Society of Virology,* University of California at Davis, Calif. 7 (1993). Finally, strain-specific resistance to potato virus Y infection has been reported in tobacco having been transformed with the NIa proteinase of potato virus Y.

To date, methods for introduction of viral resistance in plants, and especially methods for achieving resistance to potato virus Y and other economically-important viruses, have been relatively strain-specific. Moreover, there are no reports of the use of P1 gene sequences to generate resistance to any virus in potatoes or any other plant species. Accordingly, there is a need in the art for a method for conferring resistance to viral pathogens across a range of species. In addition, due to the economic importance of controlling plant pathogens, and especially plant pathogens infecting food crops, there is a need in the art for additional transgenic virus-resistant plant species and methods for making such transgenic plant species.

SUMMARY OF THE INVENTION

The present invention generally relates to transgenic plant species having resistance to infection by one or more viral plant pathogens, to materials and methods for conferring such resistance, and to materials and methods for producing said transgenic plant species. Unlike materials and methods reported in the art, transformation of plant species as taught herein confers resistance to various viruses on a wide range of different plant species and wherein a gene, the P1 gene, is used in a manner not previously reported.

Transgenic plants and methods for making and using them according to the present invention are useful to increase the viability of plant crops and to increase plant yields. Transgenic plants and methods for producing them according to the present invention reduce crop loss due to infection by viral pathogens.

In general, the present invention provides transgenic plants resistant to infection by a virus selected from the group consisting of potato virus Y, potato leaf roll virus, potato virus A, potato virus V, potato moptop virus, potato yellow dwarf virus, tobacco mosaic virus, tobacco etch virus, tobacco vein mottlng virus, tobacco ringspot virus, tobacco streak virus, tobacco yellow dwarf virus, tomato golden mosaic virus, tomato spotted wilt virus, tomato bushy stunt virus, tomato ring spot virus, tomato black ring virus, pepper ringspot virus, pepper mottle virus, pepper mild mottle virus, and pepper veinal mottle virus (collectively refereed to as "the viruses). Plant species in which resistance may be conferred include potatoes, tomatoes, tobacco, peppers, cabbage, pine, spruce, maize, wheat, rice, and birch. Generally, the resistance conferred by methods and materials according to the present invention is effective against any virus in the Potyviridae family and other phyla. Plant species capable of being infected by the viruses mentioned above are rendered resistant to one or more of the viruses upon transformation according to the methods taught herein.

In a preferred embodiment of the invention, a plant species capable of being infected by one or more of the viruses is genetically transformed with DNA encoding a P1 protein of potato virus Y or an effective portion thereof. As used herein, an effective portion of a P1 protein of potato virus Y is a portion of that protein which retains a proteolytic activity as characterized, inter alia, in Verchot, et al., Virology, 185: 527–535 (1991) and/or which retains RNA binding activity characteristic of P1. Also in a preferred embodiment of the invention, a plant capable of being pathogenically infected by one or more of the viruses is transformed with a vector comprising DNA encoding a P1 protein or an effective portion thereof. P1 vector DNA may be further transformed into a plasmid, such as a Ti-plasmid, for further transformation into a plant. However, the skilled artisan is aware of various means for transforming plants. Transgenic plant species according to the invention preferably may be transformed with DNA as shown in SEQ ID NO: 3. Suitable plants for transformation as described herein include, but are not limited to, those mentioned above. Viruses against which resistance may be conferred according to the present invention include, but are not limited to, the viruses mentioned above.

Also in a preferred embodiment of the invention, a transgenic potato is taught which has resistance to infection by potato virus Y. A transgenic potato according to the present invention may be a potato having been transformed with DNA encoding a P1 protein of potato virus Y or an effective portion thereof. A transgenic potato according to the present invention may be a potato having been transformed with DNA as shown in SEQ ED NO: 3. Also in a preferred embodiment, a potato shoot may be transformed with DNA encoding a P1 protein of potato virus Y.

In a method according to the present invention, transgenic plants are produced by transforming plantlets with DNA comprising a P1-encoding portion. The skilled artisan appreciates that any plant cell may be transformed by methods described herein. However, it is preferred to conduct transformation in plantlets (i.e., cultivars approximately four weeks old). In a preferred embodiment, P1-encoding DNA is transformed as part of a vector and may preferably be part of a plasmid, such as pHTT294, further conjugated into a Ti plasmid of *Agrobacterium tumefaciens*, which is then transformed into plant cells. Also in a preferred embodiment, the transgenic plant may be selected from the group consisting of tuber crops and, further from the group consisting of potatoes, cauliflower, tobacco, tomatoes, and carrots.

Also provided by the present invention are methods for production of transgenic plants having a resistance to potato virus Y, comprising the steps of transforming a plant with DNA encoding P1 or an effective portion thereof and cultivating the resulting transformants under normal growth conditions.

DNA comprising a region encoding an effective portion of P1 protein of potato virus Y is effective in conferring resistance to viral infection in numerous species and strains of plants. Specifically, the P1 protein of potato virus Y is useful for conferring resistance to numerous viruses which infect members of the Solanaceae family and other plant families, including potato, tobacco, and pepper species, as well as members of related families, as listed above. Accordingly, while the present invention is specifically exemplified by conferring resistance to potato virus Y infection in potatoes, the invention also may be applied to confer resistance to other viruses in other plant species as enumerated above using P1. In addition, the invention may be used to confer resistance to other viruses in potatoes. Accordingly, application of the present technology to species not specifically exemplified herein is expected to function to confer resistance to such species.

In one aspect, the invention provides a virus-resistant plant comprising plant cells transformed with a polynucleotide, the polynucleotide comprising a nucleotide sequence encoding a P1 protein of a Potyviridae virus or a portion of the P1 protein which retains P1 proteolytic activity or which binds RNA, the plant having increased resistance to infection by the virus compared to a wildtype plant of the same species which is free of cells transformed with the polynucleotide. By plant is meant any member of the plant kingdom that is susceptible to infection by viruses from the family Potyviridae, including but not limited to plants set forth above.

In a preferred embodiment, the virus-resistant plant is an angiosperm. Thus, in a related aspect, the invention includes seeds from plants of the invention, the seeds comprising plant cells transformed with the polynucleotide, such that the seeds are capable of germinating into plants that are virus-resistant. Such seeds are useful for regenerating virus-resistant offspring of plants of the invention. Such offspring themselves are intended as an aspect of the invention. The seeds of some species also are useful as food products-or as sources of food products (e.g., oils).

In a highly preferred embodiment, the virus-resistant plant is from the family Solanaceae. Virus-resistant potatoes, tomatoes, tobaccos, peppers, and the like are specifically contemplated.

In a related aspect, the invention includes commercially valuable portions of the virus-resistant plants of the invention. In addition to seeds mentioned above, the invention includes, for example, a tuber from a virus-resistant potato plant of the invention; a leaf from a virus-resistant tobacco plant of the invention; the fruits from tomato or pepper plants of the invention; and the like.

With respect to the polynucleotide comprising a nucleotide sequence encoding a P1 protein of a Potyviridae virus or a portion of the P1 protein which retains P1 proteolytic activity or which binds RNA, a preferred portion of the P1 protein is a portion comprising the portion of PVY P1 protein encoded by SEQ ID NO: 3 and set forth in SEQ ED NO: 4. It has recently been reported that the carboxyl terminus of the PVY P1 protein actually extends about 8 amino acids downstream of the sequence encoded by SEQ ED NO: 3 and set forth in SEQ ID NO: 4. Exemplary DNA and amino acid PVY P1 sequences which include 8 additional codons/residues (relative to SEQ ID NO: 3) are depicted in SEQ ID NOs: 5–6 and 7–8. Smaller fragments of P1 protein are specifically contemplated.

In a preferred embodiment, the P1-encoding polynucleotide comprises a nucleotide sequence encoding a P1 protein or portion thereof from a potyvirus, such as from the viruses listed above. Nucleotide sequence information has been reported in the art for many members of the Potyviridae family (e.g., potato virus Y, potato virus X, potato virus M, potato virus A, bean common mosaic virus, bean yellow mosaic virus, plum pox virus, pepper mottle virus, pea seed-borne mosaic virus, turnip mosaic virus, zucchini yellow mosaic virus, barley mild mosaic virus, barley mosaic virus, brome streak mosaic rymovirus, peanut stripe virus, yam mosaic virus, tobacco etch virus, and tobacco vein mottling virus), and P1 encoding sequences from these viruses are specifically contemplated. In one highly preferred embodiment, the P1 sequence is derived from potato virus Y.

In another preferred embodiment, the P1 sequence is derived from Bean Yellow Mosaic Virus (BYMV). Preferred plants for transformation with a BYMV P1 sequence include commercially important grain and forage legumes (alfalfas, clovers, wheats, barleys, rices, etc.) known to be adversely affected by BYMV infection.

In another preferred embodiment, the polynucleotide used to transform plants comprises, in addition to a nucleotide sequence encoding a P1 protein (or portion thereof), a promoter sequence operably linked to the sequence encoding the P1 protein, the promoter promoting transcription of the P1 encoding sequence in the plant. A cauliflower mosaic virus 35S promoter (CaMV 35S promoter) comprises a suitable promoter, as exemplified herein.

In another preferred embodiment, the promoter sequence is operably liked to the sequence encoding a P1 protein (or portion thereof) such that the promoter promotes transcription in the plant of an antisense RNA complementary to the P1 encoding sequence.

In a related aspect, the invention provides a method for conferring resistance to a Potyviridae virus in a plant species, comprising the steps of: (a) transforming one or more members of the plant species with a polynucleotide encoding a P1 protein from a Potyviridae virus, or a portion thereof which retains P1 proteolytic activity and which binds RNA, thereby providing transformed plants; and ( b) selecting a transformed plant having resistance to a Potyviridae virus.

In preferred embodiments, the polynucleotide further comprises a promoter sequence operably linked to the P1 encoding sequence, the promoter sequence promoting transcription in the plant of either (a) the P1 encoding sequence, or (b) an antisense RNA complementary to the P1 encoding sequence.

Similarly, the invention provides a method for conferring resistance to a Potyviridae virus in a plant species comprising the steps of: (a) transforming a plant cell or cells with a polynucleotide comprising a nucleic acid sequence encoding a P1 protein of a Potyviridae virus or a portion of the P1 protein which retains P1 proteolytic activity or which binds RNA; (b) regenerating the plant cell or cells to provide a regenerated plant; and (c) selecting a regenerated plant which expresses the nucleotide sequence encoding a P1 protein or portion thereof at an expression level which confers resistance to a Potyviridae virus. Preferred P1 encoding sequences for use in the invention and preferred plant species are summarized above.

In yet another embodiment, the invention provides a method for conferring resistance to a Potyviridae virus in a plant species comprising the steps of: (a) transforming a plant cell or cells with a polynucleotide comprising a nucleic acid sequence encoding a P1 protein of a Potyviridae virus or a portion thereof; (b) regenerating the plant cell or cells to provide a regenerated plant; and (c) selecting a regenerated plant wherein antisense RNA complementary to the nucleotide sequence encoding a P1 protein or portion thereof is produced at a level which confers resistance to a Potyviridae virus. In a preferred embodiment, the polynucleotide of step (a) further comprises a promoter sequence operably lined to the sequence encoding a P1 protein of a Potyviridae virus or a portion thereof, the promoter sequence promoting transcription in the plant of an antisense RNA complementary to the P1 encoding sequence or portion thereof.

In addition to virus-resistant plants and methods for conferring viral resistance, the present invention also provides materials for conferring resistance to viral infection in plants. For example, in one embodiment, the invention provides an isolated DNA comprising a promoter sequence operably linked to a P1 coding sequence, wherein the promoter sequence promotes transcription of the P1 coding sequence in plant cells, and wherein the P1 coding sequence encodes a P1 protein from a plant Potyviridae virus, or a portion of the P1 protein which retains P1 proteolytic activity or which binds RNA. In another embodiment, the invention provides an isolated DNA comprising a promoter sequence operably linked to a P1 coding sequence, wherein the P1 coding sequence encodes a P1 protein from a plant Potyviridae virus or a portion of the P1 protein, and wherein the promoter sequence promotes transcription of antisense RNA complementary to the P1 coding sequence or portion thereof in plant cells. Numerous exemplary members of the Potyviridae family are set forth herein. Preferably, the P1 coding sequence encodes a potyvirus P1 protein or portion thereof, e.g., the P1 coding sequence from potato virus Y. In one embodiment, a DNA of the invention is a chimeric construct wherein the promoter is derived from one species, and wherein the P1 sequence is derived from a separate and distinct species.

In yet another embodiment, the invention provides a plant transformed with an isolated DNA according to claim 25, the plant having resistance to infection from the Potyviridae virus. The invention also includes the sexually or asexually produced progeny of a plants of the invention and of plants produced according to methods of the invention, wherein the progeny have resistance to infection from the Potyviridae virus.

Additional aspects and advantages of the present invention will become apparent to the skilled artisan upon consideration of the following detailed description thereof.

DETAILED DESCRIPTION OF THE INVENTION

Figure 1:
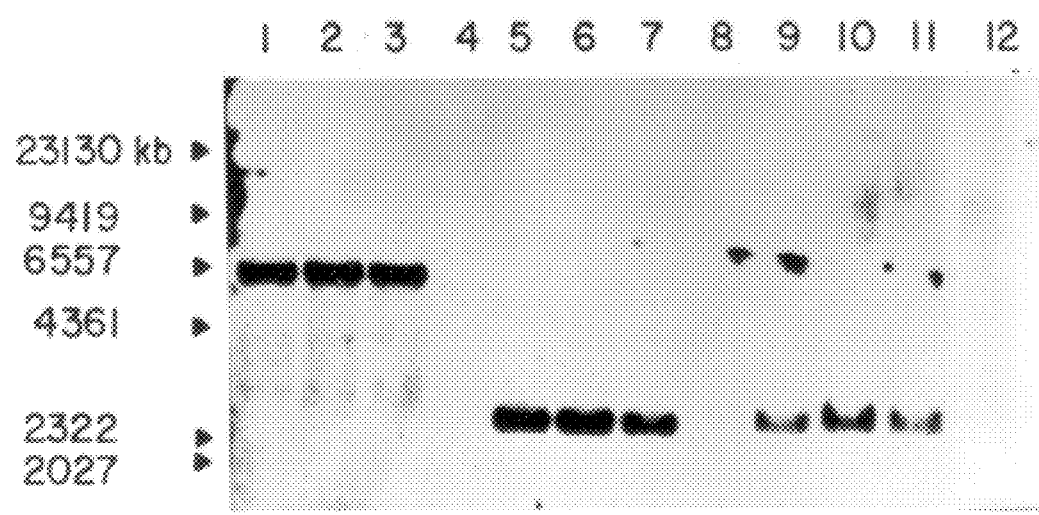
FIG. 1 represents Southern blots of HindIII (lanes 1–4); SmaI plus HindIII (lanes 5–8); and SmaI (lanes 9–12) digests of DNA from PVY-resistant and PVY-susceptible P1 transgenic PITO plants.
Figure 2:
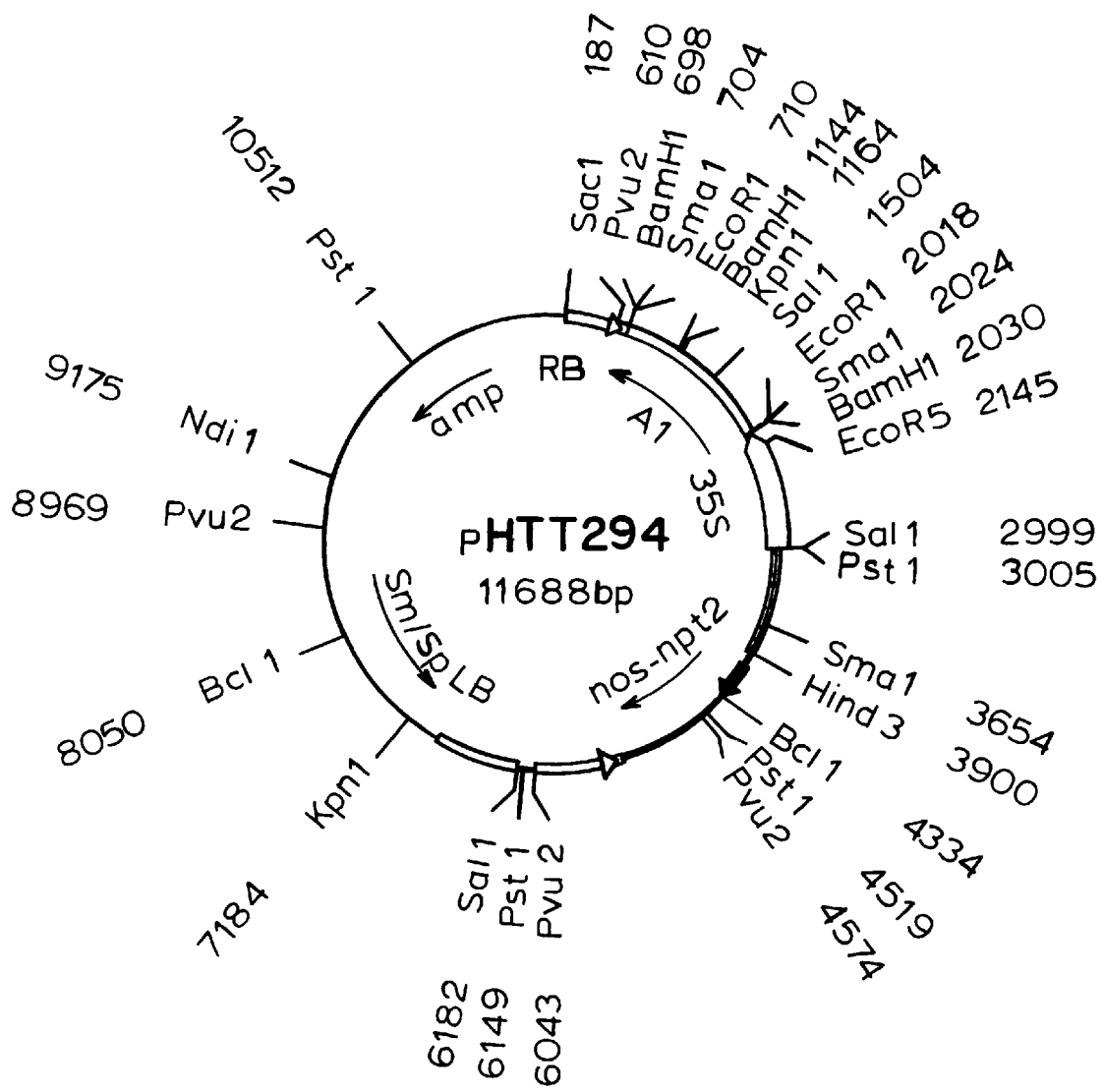
FIG. 2 schematically depicts the organization of plasmid pHTT294, wherein RB and LB represent right and left border sequences, 35S represents the CaMV 35S promoter, and the nos-npt2 gene encodes kanamycin resistance and thereby provides a selectable marker.

The present invention provides a new strategy for generating resistance against a variety of plant viruses by transformation of susceptible plants with a P1 gene of a virus from the Potyviridae family, and preferably from the potyvirus genus, such as the P1 gene from potato virus Y. The results provided in the examples below establish a high resistance to infection in transformed plants. The following Examples are illustrative of the invention and provide preferred embodiments thereof. However, it is apparent to the skilled artisan that various embodiments of the invention not specifically exemplified herein will also achieve the result of conferring resistance upon transformed plant cells.

EXAMPLE 1

Using The P1 Gene Of Potato Virus Y To Generate Transgenic Potato Plants Resistant to PVY Infection The following procedures and results demonstrate that transformation of a potato plant with the P1 gene from a wildtype potyvirus (potato virus Y) is capable of conferring resistance to potyvirus infection and damage caused by infection.

EXTRACTION OF VIRAL RNA AND SYNTHESIS OF cDNA

Numerous methods for the extraction and purification of RNA and manufacture of cDNA libraries are known. See, e.g., Sambrook, et al., *Molecular cloning: A Laboratory Manual,* 7.3–7.84 and 8.3–8.82 (1989). Consequently, any known method may be used to generate cDNA encoding a P1 protein of potato virus Y for use according to the methods taught herein.

In order to generate potato virus Y (PVY) cDNA, tobacco leaves were infected with a wild-type strain of PVY. Such a strain is reported in Gibson, et al., *Ann. Appl. Biol.,* 116: 151–156 (1990), incorporated by reference herein. A crude viral extract was prepared according to the method of Edwards, et al., *Nucl. Acids Res.,* 19: 1349 (1991), incorporated by reference herein, in order isolate total viral RNA. To extract RNA, leaf tissue (2–4 grams) was frozen in about 50 ml liquid nitrogen and was then ground to a fine powder. An equal volume of extraction buffer (200 mM Tris-HCl, pH 7.5, 250 mM NaCl, 25 mM EDTA, 0.5% SDS) was then added, mixed well, and the extracts were vortexed for 5 seconds. Extracts were then centrifuged at 13,000 rpm for 1 minute and 300 μl of the supernatant were transferred to a fresh tube. That tube was left at room temperature for about two minutes with the addition of 300 μl isopropanol. The extract was then centrifuged at 13,000 rpm for 5 minutes and the pellet was vacuum dried and dissolved in 100 μl TE (10 mM Tris, pH 8.0; 1.0 mM EDTA).

The RNA preparation obtained was used in the preparation of a cDNA library using a 1st Strand Synthesis Kit (Pharmacia) according to the manufacturer's instructions. A random hexanucleotide mixture was used to prime the RNA.

The cDNA obtained as provided above was subjected to PCR amplification using a Taq DNA polymerase (Promega). The upstream primer for amplification was 5'-GGGAATTCATATGGCAACTTACATGTCAACA-3' (SEQ ID NO: 1), which corresponds to nucleotides 185 through 205 of the PVY$^n$ (the similarity of the sequences of PVY$^n$ and PVY$^o$ allows the use of either strain for construction of PCR primers) RNA sequence reported by Robaglia et al., *J. Gen. Virol.,* 70: 935–947 (1989), with additional sequence providing EcoRI and NdeI sites. The downstream primer was 3'-GGGGATCCACTCTTGATAACTCTAGAACGTGC-5' (SEQ ID NO: 2), corresponding to nucleotides 989 through 1012 of the PVY$^n$ RNA sequence with an additional BamHI site. The amplified region corresponds to the P1 gene of the PVY strain employed, as reported by Robaglia et al. (1990). PCR was carried out using a PTC-100 Thermocycler with a programmable Thermal Controller M Research) at 92°–35°–72° C. for 30 cycles. The skilled artisan knows standard PCR protocols. See, e.g., Ausubel, et al., *Current Protocols in Molecular Biology:* §15 (1989).

The nucleotide sequence of the resulting PCR product is shown in SEQ ID NO: 3. That product was cloned into a pCR1000 cloning vector obtained from the TA Cloning System (Invitrogen) according to the manufacturer's instructions. The cloned fragment was also subcloned into a pET3a expression vector (Novagen) by ligating the NdeI and BamHI digested fragment into unique NdeI and BamHI sites in the vector. The nucleotide sequence of the cloned fragment was obtained by the dideoxy chain termination method of Sanger, *Proc. Nat'l. Acad. Sci.* (*USA*), 74: 5463–5467, using an AutoRead DNA Sequencer Kit and an A.L.F. Automated DNA Sequencer (Pharmacia Biotech).

CLONING AND SEQUENCE ANALYSES

The cloning procedure described above resulted in the production of a cDNA clone containing the entire 31 kDa open reading frame of P1 as reported by Robaglia et al. (1990). The nucleotide sequence of the cloned fragment (SEQ ID NO: 3) was confirmed to correspond to a previously published P1 sequence of PVY$^o$ (GenBank Accession No. M37180, reported in Thornbury et al., virology, 178: 573–578 (1990)) with 94.6% homology at the nucleotide level corresponding to 97% homology at the amino acid level. The translation integrity of the cloned sequence was confirmed by in vitro translation of the cloned sequence in rabbit reticulocyte lysate, which resulted in the production of a 31 kDa product as predicted from the amino acid sequence of the native protein.

AGROBACTERIUM-MEDIATED TRANSFORMATION

The cloned P1 sequence described above was inserted into unique BamHI sites in a pHTT294 plasmid (schematically depicted in FIG. 2) in sense orientation, resulting in plasmid pHTT294P1S. The pHTT294 plasmid (pHTT294P1S) containing the cloned P1 sequence was deposited with the American Type Culture Collection, 12301 Parklawn Drive, Rockville, Md. 20852, on Apr. 1, 1994, as accession number ATCC 75726. The pHTT294 plasmid, which is similar to the pHTT370 plasmid reported in Elomaa et al., *Bio/Technology,* 11:508–511 (1993), contains a cauliflower mosaic virus 35S promoter (CaMV 35S promoter), a neomycin phosphotransferase II gene (NPTII), and a transfer DNA (T-DNA) polyadenylation signal. Correct orientation of the P1 gene sequence in the plasmid was confirmed by restriction fragment analysis. That plasmid was then further conjugated into an *Agrobacterium tumefaciens* (C58C1, Van Larebece, et al., *Nature,* 252: 169–170 (1974)) Ti-plasmid (pGV3850, Zambryski, et al., *EMBO J.,* 12: 2143–2150 (1983) by triparental mating using a GJ23 helper plasmid described in Van Haute, et al., *EMBO J.,* 12: 411–417 (1983). The construct contained a kanamycin-resistance gene. Portions of stems (approximately 3–5 mm each) were excised from 4-week-old plantlets of potato cultivar PITO, a commercially-available variety of potato produced in Finland, and were transformed with the above-described Ti-plasmid. Explants were grown on MS medium (4.71 g/L MS salts; 30 g/L sucrose, 6.0 g/L agar, pH 5.2), as reported in Murashige, et al., *Physiologia Plantarum,* 15: 473–497, incorporated by reference herein, supplemented with 2.25 mg/L BAP (6-bentsylaminopurine), 0.2 mg/L NAA (α-napthaleneacetic acid), and 0.1 mM acetosyringone for 48 hours prior to inoculation with Agrobacterium.

An overnight culture of *A. tumefaciens* grown in liquid LB medium was diluted 1:10 with liquid MS medium and explants were immersed in the inoculum. Explants were then dried briefly against a sterile filter paper and incubated on MS plates at pH 5.8 with BAP and NAA for 48 hours under shaded light at 28° C. in a growth chamber. Explants were next washed with 500 mg/L cefotaxime and placed on fresh MS medium containing cefotaxime in the same concentration as in the wash. Ten days later, explants were transferred onto MS medium (pH 5.8) containing 75 mg/L kanamycin and grown for 7 days. Finally, the explants were transferred onto MS medium (pH 5.8) supplemented with 2.25 mg/L BAP, 35.0 mg/L gibberellic acid and 75 mg/L kanamycin. Shoots regenerated approximately 28–35 days after agroinfection.

INOCULATION OF TRANSGENIC PLANTS WITH PVY

In vitro-derived potato plants were transplanted into soil and grown in a greenhouse under natural daylight extended and supplemented by fluorescent illumination with a photoperiod of 18 hours. Daily mean minimum temperature was 23° C. and daily mean maximum temperature was 27° C. Sap was extracted from the uppermost fully-expanded leaves of $PVY^o$-infected *Nicotiana tabacum* L. cv. Samsun, diluted 1:3 with distilled water, and rubbed onto carborundum-dusted leaves of 6-week-old potato plants. Three plants of each of the P1-transgenic lines were inoculated. Non-transformed plants of PITO were included as controls.

Two uppermost fully-expanded leaves were tested for PVY 14 and 21 days after inoculation using the direct double antibody sandwich enzyme-linked immunosorbent assay (DAS-ELISA) using p-nitrophenyl as substrate. Antibodies for the assay (anti-PVY antibody and anti-PVY antibody-alkaline phosphate conjugate) were obtained from Boehringer Mannheim. Absorbencies were recorded at 405 nm using an ELISA reader (Titertek Multiscan). Serial dilutions of purified $PVY^o$ were used as a standard in ELISA tests.

SCREENING OF TRANSGENIC PLANTS

Samples of leaf tissue (30–40 mg) from plants regenerated on a kanamycin-containing selection medium were screened for expression of the NPTII protein using the method of McDonnell, et al., *Plant Mol. Biol. Rep.*, 5: 380–386 (1987), incorporated by reference herein. The NPTII protein is neomycin phosphotransferase II which confers kanamyci resistance. Leaf tissue (30–40 mg) was ground in an Eppendorf tube, to which 30–40 µl extraction buffer (20% glycerol, 125 mM Tris-Hcl, pH 6.8, 10% β-mercaptoethanol, 0.2% SDS) was added. After grinding, tubes were vortexed for 10 seconds and placed on ice. The tubes were then centrifuged for 10 minutes at 15,600×g at room temperature and the resulting supernatant was transferred to a new tube. In an Eppendorf tube, 5 µl of each sample extract and 5 µl of an assay mixture (0.03 mM kanamycin, 1.48 mM ATP, 18 mM NaF, 10 µCi gamma-32-labelled phosphorus) were mixed and incubated for 20 minutes at 37° C. Samples were then centrifuged briefly and 5 µl of each sample was spotted onto a dried Whatman™ P81 (cellulose phosphate) paper which had been soaked in a solution of 20 mM ATP and 100 mM pyrophosphatase. After the spots had dried, the paper was washed for 2 minutes in 10 mM sodium phosphate buffer at pH 7.5 and 80° C. The blots were then washed in 10 mM sodium buffer at room temperature for 10 minutes, a step which was repeated 3–5 times. Finally, the blots were dried and exposed to x-ray film for 16 to 48 hours.

Genomic DNA was then isolated from leaf tissue of the transformants and control plants using the procedure of Dellaporta, et al., *Plant Mol. Biol.*, 15: 39–47 (1983), incorporated by reference herein, including phenol-chloroform and CTAB extractions. Specifically, isolation of genomic DNA was accomplished by weighing 2–4 g potato leaves, which were then ground in liquid nitrogen to a fine powder using a mortar and pestle. The powder was then transferred to a 50 ml centrifuge tube containing 20 ml extraction buffer (500 mM NaCl, 100 mM Tris-HCl, pH 8.0, 50 mM EDTA). An aliquot of 2.7 ml of 10% SDS was then added and the tube was shaken and incubated at 65° C. for 30 minutes. A ⅓ volume of 5M potassium acetate was then added and mixed well. The tube was then placed on ice for 30 minutes, after which it was centrifuged at 20,000×g for 15 minutes at 4° C. The supernatant was then poured through cheesecloth and a 0.7 volume of isopropanol was added. The tube was then placed on ice for 30 minutes and subsequently centrifuged at 1000×g for 10 minutes. The pellet was dissolved in 2 ml TE overnight at 4° C. The pellet was then incubated at 37° C. for 30 minutes upon addition of 4 µl RNAase. Phenol-chloroform extraction was then performed (2–4 times) followed by CTAB extraction (1% CTAB, 1.25M NaCl, incubated 10 minutes at 60° C.), followed by two chloroform extractions. Two volumes of ethanol were then added and the tube was placed on ice for 15 minutes. Finally, the tube was centrifuged at 3000×g for 10 minutes, the resulting pellet was washed with 75% ethanol and then dried in a Speed Vac and dissolved in 250 µl to 500 µl TE buffer.

The cloned P1 sequence was radioactively labeled with $\alpha^{32}P$ CTP according to the instructions of the manufacturer (Oligolabelling Kit, Pharmacia) and was used to probe HindIII, HindIII plus SmaI, and SmaI digested DNA samples.

ANALYSIS OF TRANSGENIC PLANTS

Randomly-selected transformants, regenerated on medium (MS medium supplemented with 2.25 mg/L BAP, 35.0 mg/L gibberellic acid) containing kanamycin (75 mg/L), were allowed to root on a kanamycin-free medium. Seventy-one of the rooted $R_0$ plantlets were assayed for neomycin phosphotransferase activity (NPTII) by methods described in McDonnell et al., supra. Thirty-five of the tested seedlings were NPTII positive and represented 27 independent cell lines. Growth and appearance of the NPTII positive plants were similar to those of non-transformed control plants of PITO.

Nine of the NPTII positive $R_0$ plants were assayed for vial resistance by ELISA. The results are summarized in Table 1; wherein mean $PVY^o$ concentrations (µg $PVY^o$/g potato leaves) in each of the three copies (a,b,c) of P1 transgenic lines, and in untransformned PITO control (inoculated and uninoculated) were measured 14 and 21 days post inoculation (dpi). In all ELISA experiments, serial dilutions of purified $PVY^o$ was used as standards.

TABLE 1

PVY$_O$ (μg/g leaves)

| Cell Line | | 14 dpi | 21 dpi |
|---|---|---|---|
| Experiment 1: | | | |
| 1002SI1 | a | 0,0 | ND |
| | b | 0,0 | ND |
| | c | 0,0 | ND |
| SI0319-1 | a | 561,0 | ND |
| | b | 510,0 | ND |
| | c | 1122,0 | ND |
| PITO control (inoculated) | a | 244,8 | ND |
| | b | 142,8 | ND |
| PITO control (uninoculated) | a | 0,0 | ND |
| | b | 0,0 | ND |
| Experiment 2: | | | |
| SI0626-1 | a | 112,2 | 127,5 |
| | b | 260,1 | 89,4 |
| | c | 484,5 | 255,0 |
| SI0319-3 | a | 237,0 | ND |
| | b | 99,0 | ND |
| | c | 330,0 | ND |
| SI0605-1 | a | 0,0 | ND |
| | b | 264,0 | ND |
| | c | 114,0 | ND |
| PITO control (inoculated) | a | 210,0 | 107,1 |
| | b | 109,8 | 188,7 |
| PITO control (uninoculated) | a | 0,0 | 0,0 |
| | b | 0,0 | 0,0 |
| Experiment 3: | | | |
| SI0601-2 | a | 0,0 | 64,8 |
| | b | ND | 0,0 |
| | c | 76,5 | 54,0 |
| SI0305-1 | a | 0,0 | 0,0 |
| | b | 0,0 | 0,0 |
| | c | 0,0 | 0,0 |
| SIII1113-1 | a | 0,0 | 0,0 |
| | b | 0,0 | 0,0 |
| | c | 0,0 | 0,0 |
| SI0523-1 | a | ND | 0,0 |
| | b | ND | 18,3 |
| | c | ND | 17,7 |
| PITO control (inoculated) | a | 45,9 | 125,4 |
| | b | 178,9 | 57,0 |
| PITO control (unioculated) | a | 0,0 | 0,0 |
| | b | 0,0 | 0,0 |

ND = not determined

As shown in Table 1, no PVY was detected in the P1-transformants, 1002SI1, SIII 1113-1 and SI0305-1, representing three independent lines, 21 days after inoculation. Those plants also remained symptomless. In contrast, other tested lines transformed with P1 showed mosaic symptoms and had high PVY titres similar to those of nontransformed PVY-infected PITO plants. Two of the NPTII positive R$_0$ plants, one resistant plant, 1002SI1, and one susceptible plant, S10319-1, were analyzed by Southern blot hybridization using the cloned P1 sequence as a probe. Southern analysis confirmed the presence of the transgene in the genome of the resistant plant as a single insert, but no signal was detected in Southern analysis of the susceptible plant. The results are shown in FIG. 1; wherein lanes 1–3, 5–7, and 9–11 are blots from three different copies of a resistant strain; and lanes 4, 8, and 12 are blots from a susceptible strain.

EXAMPLE 2

Using the P1 Gene in Anti-sense Orientation to Generate Transgenic Potato Plants Resistant to PVY Infection The PVY P1 gene segment described in Example 1 also was transformed in an antisense orientation into potato cultivar PITO. The P1 construct used for transformation was essentially identical to the construct described in the preceding example and deposited with the ATCC, except that the P1 insert was inserted into the unique BamHI site of the pHTT294 plasmid in an anti-sense orientation. Correct orientation of the P1 gene sequence was confirmed via restriction digestion using NdeI and HindIII enzymes, resulting in fragments of approximately 575 base pairs (bp), 1915 bp, 3217 bp, and 5150 bp (comprared to fragments of 575 bp, 1676 bp, 3456 bp, and 5150 bp from the sense-oriented construct). Transformation and screening of potato plants, viral inoculations, and virus tests were performed as described in the preceding example and in Pehu et al., *American Potato J.*, 72:523–532 (1995). The presence of the P1 antisense RNA in transgenic lines was confirmed by Northern analysis using a strand-specific RNA probe. As the results in Table 2 demonstrate, five independent lines of antisense-transformed PITO plant cultivars showed resistance against potato virus Y, both in sap and in graft inoculations. Twenty-three other transgenic lines showed infection symptoms and had high virus titres.

TABLE 2

ELISA test results (absorbance at A405, mean and standard deviation) of five P1 antisense transgenic PITO potato lines (3 copies each) and of nontransformed control PITO plants.

| | sap-inoculation | | | | graft-inoculation | | | |
|---|---|---|---|---|---|---|---|---|
| Plant Line | 14 dpi A 405 | STDEV | 21 dpi A 405 | STDEV | 21 dpi N 405 | STDEV | 35 dpi A 405 | STDEV |
| AII 1814-1 | 0,007 | 0,008 | 0,001 | 0,002 | 0,000 | 0,000 | 0,016 | 0,002 |
| AI 0306-3 | 0,000 | 0,000 | 0,003 | 0,005 | 0,004 | 0,007 | 0,023 | 0,003 |
| AI 0623-2 | 0,009 | 0,008 | 0,001 | 0,002 | 0,005 | 0,005 | 0,018 | 0,007 |
| AI 1139-1 | 0,000 | 0,000 | 0,000 | 0,001 | 0,003 | 0,005 | 0,027 | 0,003 |
| AII 1813-1 | 0,007 | 0,004 | 0,002 | 0,003 | 0,000 | 0,000 | 0,010 | 0,005 |
| Pito, infected | 1,397 | 0,105 | 1,262 | 0,077 | 1,259 | 0,323 | 1,271 | 0,255 |
| Pito, healthy | 0,033 | 0,045 | 0,008 | 0,008 | 0,005 | 0,004 | 0,014 | 0,011 |

The foregoing results demonstrate that resistance to viral infection can be conferred by transformation of susceptible plants with the P1 gene of a potyviridae virus, in anti-sense conformation.

EXAMPLE 3

Using the P1 Gene of Potato Virus Y to Generate Transgenic Tobacco Plants Resistant to PVY Infection Using the P1 gene constructs and Agrobacterium strains described in Examples 1 and 2, *Nicotiana tabacum* SR1 plants were transformed with P1 gene both in sense and in antisense orientation. Transformations of tobacco were performed using an Agrobacterium-mediated leaf disk transformation-regeneration method, essentially as described in Horsch et al., *Science*, 227:1229–1231 (1985), incorporated by reference herein. Independent primary transformants were rooted on media containing 100 mg/l kanamycin and subsequently transplanted into soil. Two weeks after transplantation, the two uppermost leaves of each plant (3 plants for independent transformant line) were inoculated with sap from potato virus Y-infected tobacco. Eighteen days after inoculation, plants were tested for PVY° concentration with DAS-ELISA as described above, and symptoms were scored. Four out of seventeen independent antisense-transformed lines (AI-2, AI-4, AI-12, AI-22) and three out of twenty independent sense-transformed lines (SI-1, SI-11, SI-29) did not shown any symptoms and had low absorbance values in ELISA tests (mean absorbance measurements of 0,028–0,064, compared to 0,041 for healthy control tobacco plants), the remaining antisense-transformed and sense-transformed lines showing typical PVY infection symptoms and higher absorbance values in the ELISA tests (Tables 3–5).

TABLE 3

| AI ANTISENSE | symptoms | A 405, 18 dpi | stdev |
|---|---|---|---|
| AI-1 | + | 1,226 | |
| AI-2 | − | 0,047 | 0,023 |
| AI-4 | − | 0,048 | 0,036 |
| AI-5 | + | 0,754 | |
| AI-11 | + | 1,716 | |
| AI-12 | − | 0,043 | 0,021 |
| AI-13 | + | 1,020 | |
| AI-14 | + | 1,131 | |
| AI-19 | + | 1,771 | |
| AI-20 | + | 1,191 | |
| AI-22 | − | 0,028 | 0,009 |
| AI-23 | + | 1,214 | |
| AI-24 | + | 1,457 | |
| AI-26 | + | 1,162 | |
| AI-27 | + | 0,733 | |
| AI-28 | + | 1,060 | |
| AI-29 | + | 1,305 | |
| healthy tobacco | | 0,041 | 0,020 |

TABLE 4

| SI SENSE | symptoms | A 405, 18 dpi | stdev |
|---|---|---|---|
| SI-1 | − | 0,057 | 0,015 |
| SI-3 | − | 0,122 | 0,031 |
| SI-4 | + | 1,156 | |
| SI-5 | + | 1,304 | |
| SI-6 | − | 0,147 | 0,147 |
| SI-7 | + | 1,293 | |

TABLE 4-continued

| SI SENSE | symptoms | A 405, 18 dpi | stdev |
|---|---|---|---|
| SI-8 | + | 0,933 | |
| SI-9 | − | 0,134 | 0,115 |
| SI-11 | − | 0,064 | 0,021 |
| SI-14 | + | 1,178 | |
| SI-15 | + | 1,498 | |
| SI-16 | + | 0,657 | 1,010 |
| SI-17 | + | 1,430 | |
| SI-18 | + | 1,540 | |
| SI-19 | + | 1,345 | |
| SI-21 | + | 1,963 | |
| SI-22 | + | 1,095 | |
| SI-26 | − | 0,042 | 0,020 |
| SI-28 | + | 1,236 | |
| SI-29 | − | 0,031 | 0,004 |

TABLE 5

| K3-CONTROL | symptoms | A 405, 18 dpi |
|---|---|---|
| K3-1 | + | 0,920 |
| K3-2 | + | 1,139 |
| K3-3 | + | 1,171 |
| K3-5 | + | |
| K3-7 | + | |
| K3-8 | + | |
| K3-10 | + | |
| K3-11 | + | |
| K3-12 | + | |
| K3-13 | + | |
| K3-14 | + | |
| K3-15 | + | |
| K3-18 | + | |
| K3-19 | + | |
| K3-20 | + | |
| K3-22 | + | |
| K3-25 | + | |
| K3-26 | + | |
| K3-29 | + | |
| K3-30 | + | |

A 405=absorbance at 405 nm; stdev=standard deviation; antisense transformed plants having PVY P1 gene in anti-sense orientation; sense=transformed plants having PVY P1 gene in sense orientation; K3=control plants transformed with empty plasmid but not with P1 gene.

The foregoing results provide an indication that transformation of multiple susceptible plant species with the P1 gene from a Potyviridae virus, in sense or antisense orientation, is capable of conferring viral resistance.

EXAMPLE 4

Transformation of Plants with P1 Gene Sequences Containing Additional 3' Coding Sequence Recently it has been reported that the cleavage site between the P1 protein and the Helper Component Protease protein (which lies immediately downstream from the P1 gene in the PVY genome) is eight amino acids further downstream than had been reported previously (i.e., the PVY P1 protein is 8 amino acids longer at its carboxy terminus). Significantly, all conserved motifs believed to be necessary for, e.g., P1 proteolytic activity, are located within the P1 sequence that is set forth in SEQ ID NO: 3 and that was used in the preceding examples to confer viral resistance. The following procedure is used to demonstrate that the putative complete P1 protein sequence, including the eight additional amino acids, may be used in an identical manner to confer viral resistance in plants.

The procedures described in the foregoing examples are repeated using a putative complete P1 coding sequence. As explained above, genomic sequence information has been reported in the art for numerous viruses in the Potyviridae family. Such sequences are preferred sequences for generating a complete P1 gene for insertion into a pHTT294 plasmid or other suitable plasmid for transformation (in sense or antisense orientation). Preferred procedures for generating complete P1 gene sequences are PCR procedures, using synthetic PCR primers made from reported genomic sequence information and using nucleic acid from viral isolates. Alternatively, polynucleotides having P1 seqeunces reported in the art are produced synthetically. Exemplary complete PVY P1 gene and amino acid sequences, derived from the sequences reported by Robaglia et al. (GenBank Accession No. D00441) and Thornbury et al. (GenBank Accession No. M37180), are set forth in SEQ ID NOs: 5–6 and 7–8, respectively.

Transformation, plant regeneration, viral resistance screening, and the like are performed essentially as described in the preceding examples to demonstrate that viral resistance is conferred via transformation with a complete PVY P1 gene sequence.

EXAMPLE 5

Transformation of Plants with P1 Gene Fragments to Confer Viral Resistance

To demonstrate that P1 gene fragments, in sense or antisense orientation, may be used to confer viral resistance in plants, the procedures described in Examples 1–3 are repeated using portions of the P1 sequences reported herein or reported in the art. For example, portions of the sequences reported in SEQ ID NOs: 3, 5, or 7 are employed. Exemplary P1 gene fragments for screening are contiguous fragments of, e.g., about 25, 50, 100, 150, 200, 250, 300, 350, 400, 450, 500, 550, 600, 650, 700, 750, or 800 base pairs from a reported P1 sequence. Preferred procedures for generating P1 gene fragments are restriction digestion of complete or nearly complete P1 clones; PCR procedures, using synthetic PCR primers made from reported genomic sequence information and using nucleic acid from viral isolates; and automated synthetic procedures known in the art. In a preferred embodiment, the fragments selected contain gene sequences from the 3' portion of the P1 gene, as this portion of the gene exhibits greater similarity between potyvirus species.

P1 gene fragments synthesized as described above are cloned (in sense or antisense orientation) into a suitable vector for transformation, such as the vector employed in Examples 1–3. Transformation, plant regeneration, viral resistance screening, and the like are performed essentially as described in the preceding examples to determine those P1 gene fragments which confer viral resistance when used to transform suitable plant hosts.

We claim:

1. A virus-resistant plant comprising plant cells transformed with a polynucleotide, said polynucleotide comprising a nucleotide sequence encoding a P1 protein of a potato virus Y or comprising a fragment of said P1-encoding nucleotide sequence effective to confer virus resistance to said plant, said plant having increased resistance to infection by said potato virus Y compared to a wildtype plant of the same species which is free of cells transformed with said polynucleotide.

2. A virus-resistant plant according to claim 1 wherein said plant is an angiosperm.

3. A seed from a plant according to claim 2, said seed comprising plant cells transformed with said polynucleotide.

4. A virus-resistant plant according to claim 1 wherein said plant is from the family Solanaceae.

5. A virus-resistant plant according to claim 1 wherein said plant is selected from the group consisting of tobacco and potato.

6. A tuber from a potato plant according to claim 5, wherein said tuber comprises plant cells transformed with said polynucleotide.

7. A leaf from a tobacco plant according to claim 5, wherein said leaf comprises transformed with said polynucleotide.

8. The virus-resistant plant according to claim 1, wherein said polynucleotide comprises the P1 protein encoding sequence shown in SEQ ID NO: 3.

9. A virus-resistant plant according to claim 1 wherein said polynucleotide further comprises a promoter sequence operably linked to said nucleotide sequence or to said fragment, said promoter sequence promoting transcription of said nucleotide sequence or said fragment in said plant.

10. A virus-resistant plant according to claim 1 wherein said polynucleotide further comprises a promoter sequence operably linked to said nucleotide sequence or to said fragment, said promoter sequence promoting transcription in said plant of RNA that is complementary to said P1 encoding nucleotide sequence or complementary to sad fragment.

11. A method for conferring resistance to a Potyviridae virus in a plant, comprising the steps of:
   transforming one or more plants with a polynucleotide comprising a nucleotide sequence encoding a P1 protein from a potato virus Y, or comprising a fragment of said P1-encoding nucleotide sequence effective to confer virus resistance to said plant, thereby providing transformed plants; and
   selecting a transformed plant having resistance to said potato virus Y, thereby providing a plant with resistance to a Potyviridae virus.

12. A method according to claim 11 wherein sad polynucleotide further comprises a promoter sequence operably linked to said nucleotide sequence or to said fragment, said promoter sequence promoting transcription of said nucleotide sequence or said fragment in said plant.

13. A method according to claim 11 wherein said polynucleotide further comprises a promoter sequence operably linked to said nucleotide sequence or to said fragment, said promoter sequence promoting transcription in said plant of RNA that is complementary to said P1 encoding nucleotide sequence or complementary to said fragment.

14. A method for conferring resistance to a Potyviridae virus in a plant comprising the steps of:
   transforming a plant cell with a polynucleotide comprising a nucleic acid sequence encoding a P1 protein of a potato virus Y or comprising a fragment of said P1-encoding nucleotide sequence effective to confer virus resistance to said plant;
   regenerating a plant from said plant cell to provide a regenerated plant; and
   selecting a regenerated plant which expresses said nucleotide sequence or said fragment at an expression level which confers resistance to said potato virus Y, thereby providing a plant with resistance to a Potyviridae virus.

15. A method according to claim 14 wherein said plant species is from the family Solanaceae.

16. A method for conferring resistance to a Potyviridae virus in a plant comprising the steps of:
   transforming a plant cell with a polynucleotide comprising a nucleic acid sequence encoding a P1 protein of a potato virus Y or comprising a fragment of said P1-encoding nucleotide sequence effective to confer virus resistance to said plant;
   regenerating a plant from said plant cell to provide a regenerated plant; and
   selecting a regenerated plant wherein RNA complementary to said nucleotide sequence or complementary to said fragment is produced at a level which confers resistance to said potato virus Y, thereby providing a plant with resistance to a Potyviridae virus.

17. A method according to claim 16 wherein said polynucleotide further comprises a promoter sequence operably linked to said nucleotide sequence or to said fragment, said promoter sequence promoting transcription in said plant of RNA complementary to said P1 encoding nucleotide sequence or complementary to said fragment.

18. An isolated DNA comprising a promoter sequence operably linked to a polynucleotide, said polynucleotide comprising a nucleotide sequence encoding a P1 protein from a potato virus Y or comprising a fragment of said nucleotide sequence effective to confer potato virus Y resistance to a plant transformed with said isolated DNA, wherein said promoter sequence promotes transcription of said polynucleotide in plant cells.

19. An isolated DNA comprising a promoter sequence operably linked to a nucleotide sequence, wherein said nucleotide sequence encodes a P1 protein from a potato virus Y or encodes a fragment of said P1 protein, wherein said promoter sequence promotes transcription of RNA complementary to said nucleotide sequence in plant cells, and wherein said isolated DNA is effective to confer potato virus Y resistance to a plant transformed with said isolated DNA.

20. A plant transformed with an isolated DNA according to claim 19, said plant having resistance to infection from said potato virus Y.

21. The sexually or asexually produced progeny of a plant according to claim 20, wherein said progeny have resistance to infection from said potato virus Y.

22. The sexually or asexually produced progeny of a plant according to claim 1, wherein said progeny have said increased resistance to infection from said virus.

23. A plant produced by the method of claim 14, or the sexually or asexually produced progeny thereof that express said nucleotide sequence or said fragment at an expression level which confers resistance to said potato virus Y.

24. A plant produced by the method of claim 16, or the sexually or asexually produced progeny thereof that express RNA complementary to said nucleotide sequence or complementary to said fragment and that are resistant to said potato virus Y.

25. A plant transformed with an isolated DNA according to claim 18, said plant having resistance to infection from said potato virus Y.

26. A virus-resistant plant according to claim 26 wherein said plant is an angiosperm.

27. A seed from a plant according to claim 27, said seed comprising plant cells transformed with said DNA.

28. A virus-resistant plant according to claim 20 wherein said plant is an angiosperm.

29. A seed from a plant according to claim 29, said seed comprising plant cells transformed with said DNA.

30. A virus-resistant plant according to claim 29 wherein said plant is from the family Solanaceae.

31. A plant part selected from the group consisting of a tuber from a potato plant according to claim 30 or a leaf from a tobacco plant according to claim 30, wherein said plant part comprises cells transformed with said DNA.

\* \* \* \* \*

UNITED STATES PATENT AND TRADEMARK OFFICE
CERTIFICATE OF CORRECTION

PATENT NO.   : 5,968,828
DATED        : October 19, 1999
INVENTOR(S)  : Pehu et al.

It is certified that error appears in the above-identified patent and that said Letters Patent is hereby corrected as shown below:

<u>Column 29,</u>
Line 20, delete "sad" and insert -- said --.

<u>Column 30,</u>
Line 46, delete "26" and insert -- 25 --.
Line 48, delete "27" and insert -- 26 --.
Line 52, delete "29" and insert -- 28 --.
Line 54, delete "29" and insert -- 28 --.

Signed and Sealed this

Eleventh Day of March, 2003

JAMES E. ROGAN
*Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

GGGAATTCAT ATGGCAACTT ACATGTCAAC A      31

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CGTGCAAGAT CTCAATGAGT CTCACCTAGG GG      32

(2) INFORMATION FOR SEQ ID NO:3:

(i) SEQUENCE CHARACTERISTICS:

(A) LENGTH: 828 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..828

(xi) SEQUENCE DESCRIPTION: SEQ ID NO:3:

```
ATG GCA ACT TAC ATG TCA ACA ATC TGT TTC GGT TCG TTT GAA TGC AAG        48
Met Ala Thr Tyr Met Ser Thr Ile Cys Phe Gly Ser Phe Glu Cys Lys
 1               5                  10                  15

CTA CCA TAC TCA CCC GCC TCT TGC GGG CAT ATT GCG AAG GAA CGA GAA        96
Leu Pro Tyr Ser Pro Ala Ser Cys Gly His Ile Ala Lys Glu Arg Glu
                20                  25                  30

GTG CTG GCT TCC GTT GAT CCT TTT GCA GAT CTG GAA ACA CAA CTT AGT       144
Val Leu Ala Ser Val Asp Pro Phe Ala Asp Leu Glu Thr Gln Leu Ser
             35                  40                  45

GCA CGA TTG CTC AAG CAA GAA TAT GCT ACT GTT CGT GTG CTC AAG AAC       192
Ala Arg Leu Leu Lys Gln Glu Tyr Ala Thr Val Arg Val Leu Lys Asn
 50                  55                  60

GGT ACT CTT ACG TAC CGA TAC AAG ACT GAT GCC CAG ATA ACG CGC ATC       240
Gly Thr Leu Thr Tyr Arg Tyr Lys Thr Asp Ala Gln Ile Thr Arg Ile
 65                  70                  75                  80

CAG AAG AAA CTG GAA AGG AAG GAT AGG GAA GAA TAT CAC TTC CAG ATG       288
Gln Lys Lys Leu Glu Arg Lys Asp Arg Glu Glu Tyr His Phe Gln Met
                85                  90                  95

GCA GCT CCT AGT ATT GTG TCA AAA ATT ACT ATA GCT GGT GGA GAT CCT       336
Ala Ala Pro Ser Ile Val Ser Lys Ile Thr Ile Ala Gly Gly Asp Pro
            100                 105                 110

CCA TCA AAG TCT GAG CCA CAA GCA CCA AGA GGT ATC ATT CAT ACA ACT       384
Pro Ser Lys Ser Glu Pro Gln Ala Pro Arg Gly Ile Ile His Thr Thr
        115                 120                 125

CCA AGG GTG CGT AAA GTC AAG ACA CGC CCC ATA ATA AAG TTG ACA GAA       432
Pro Arg Val Arg Lys Val Lys Thr Arg Pro Ile Ile Lys Leu Thr Glu
    130                 135                 140

CCG GAG ATG GAT CAT CTC ATT AAG CAG GTG AAG CAG ATT ATG TCG GGG       480
Pro Glu Met Asp His Leu Ile Lys Gln Val Lys Gln Ile Met Ser Gly
145                 150                 155                 160

AAG AGA GGG TCT GTT CAC TTA ATT AGT AGA AAG ACC ACC CAT GTT CAA       528
Lys Arg Gly Ser Val His Leu Ile Ser Arg Lys Thr Thr His Val Gln
                165                 170                 175

TAT AAG GAG ATA CTT GGT GCA ACT CGC GCA GCG GTT CGA ACT GCA CAT       576
Tyr Lys Glu Ile Leu Gly Ala Thr Arg Ala Ala Val Arg Thr Ala His
            180                 185                 190

ATG CTG GGC TTG CGA CGG AGA GTG GAC TTC CGA TGT GAT ATG TGG ACA       624
Met Leu Gly Leu Arg Arg Arg Val Asp Phe Arg Cys Asp Met Trp Thr
        195                 200                 205

GTT GGA CTT TTG CAA CGT CTC GCT CGG ACG GAC AAA TGG TCC AAT CAA       672
Val Gly Leu Leu Gln Arg Leu Ala Arg Thr Asp Lys Trp Ser Asn Gln
    210                 215                 220

GTC CGC ACT ATC AAC ATA CGA AAG GGT GAT AGT GGA GTC ATC TTG AAC       720
Val Arg Thr Ile Asn Ile Arg Lys Gly Asp Ser Gly Val Ile Leu Asn
225                 230                 235                 240

ACA AAA AGT CTC AAA GGC CAC TTT GGT AGA AGT TCA GGA GAC TTG TTC       768
Thr Lys Ser Leu Lys Gly His Phe Gly Arg Ser Ser Gly Asp Leu Phe
                245                 250                 255

ATA GTG CGT GGA TCA CAC GAA GGG AAA TTG TAC GAT ACA CGT TCT AGA       816
Ile Val Arg Gly Ser His Glu Gly Lys Leu Tyr Asp Thr Arg Ser Arg
            260                 265                 270
```

```
GTT ACT CAG AGT                                                          828
Val Thr Gln Ser
        275
```

(2) INFORMATION FOR SEQ ID NO:4:

(i) SEQUENCE CHARACTERISTICS:
        (A) LENGTH: 276 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Thr Tyr Met Ser Thr Ile Cys Phe Gly Ser Phe Glu Cys Lys
 1               5                  10                  15

Leu Pro Tyr Ser Pro Ala Ser Cys Gly His Ile Ala Lys Glu Arg Glu
            20                  25                  30

Val Leu Ala Ser Val Asp Pro Phe Ala Asp Leu Glu Thr Gln Leu Ser
        35                  40                  45

Ala Arg Leu Leu Lys Gln Glu Tyr Ala Thr Val Arg Val Leu Lys Asn
    50                  55                  60

Gly Thr Leu Thr Tyr Arg Tyr Lys Thr Asp Ala Gln Ile Thr Arg Ile
65                  70                  75                  80

Gln Lys Lys Leu Glu Arg Lys Asp Arg Glu Glu Tyr His Phe Gln Met
                85                  90                  95

Ala Ala Pro Ser Ile Val Ser Lys Ile Thr Ile Ala Gly Gly Asp Pro
            100                 105                 110

Pro Ser Lys Ser Glu Pro Gln Ala Pro Arg Gly Ile Ile His Thr Thr
        115                 120                 125

Pro Arg Val Arg Lys Val Lys Thr Arg Pro Ile Ile Lys Leu Thr Glu
130                 135                 140

Pro Glu Met Asp His Leu Ile Lys Gln Val Lys Gln Ile Met Ser Gly
145                 150                 155                 160

Lys Arg Gly Ser Val His Leu Ile Ser Arg Lys Thr Thr His Val Gln
                165                 170                 175

Tyr Lys Glu Ile Leu Gly Ala Thr Arg Ala Ala Val Arg Thr Ala His
            180                 185                 190

Met Leu Gly Leu Arg Arg Arg Val Asp Phe Arg Cys Asp Met Trp Thr
        195                 200                 205

Val Gly Leu Leu Gln Arg Leu Ala Arg Thr Asp Lys Trp Ser Asn Gln
210                 215                 220

Val Arg Thr Ile Asn Ile Arg Lys Gly Asp Ser Gly Val Ile Leu Asn
225                 230                 235                 240

Thr Lys Ser Leu Lys Gly His Phe Gly Arg Ser Ser Gly Asp Leu Phe
                245                 250                 255

Ile Val Arg Gly Ser His Glu Gly Lys Leu Tyr Asp Thr Arg Ser Arg
            260                 265                 270

Val Thr Gln Ser
        275
```

(2) INFORMATION FOR SEQ ID NO:5:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..852

(xi) SEQUENCE DESCRIPTION: SEQ ID NO:5:

```
ATG GCA ACT TAC ATG TCA ACA ATC TGT TTT GGT TCG TTT GAA TGC AAG       48
Met Ala Thr Tyr Met Ser Thr Ile Cys Phe Gly Ser Phe Glu Cys Lys
 1               5                  10                  15

CTA CCA TAC TCA CCA GCC TCT TGC GAG CAT ATT GTG AAG GAA CGA GAA       96
Leu Pro Tyr Ser Pro Ala Ser Cys Glu His Ile Val Lys Glu Arg Glu
                20                  25                  30

GTG CCG GCT TCC GTT GAT CCT TTC GCA GAT CTG GAA ACA CAA CTT AGT      144
Val Pro Ala Ser Val Asp Pro Phe Ala Asp Leu Glu Thr Gln Leu Ser
             35                  40                  45

GCA CGA TTG CTC AAG CAA AAA TAT GCT ACT GTT CGT GTG CTC AAA AAC      192
Ala Arg Leu Leu Lys Gln Lys Tyr Ala Thr Val Arg Val Leu Lys Asn
         50                  55                  60

GGT ACT TTT ACG TAC CGA TAC AAG ACT GAT GCC CAG ATA ATG CGC ATT      240
Gly Thr Phe Thr Tyr Arg Tyr Lys Thr Asp Ala Gln Ile Met Arg Ile
 65                  70                  75                  80

CAG AAG AAA CTG GAG AGG AAG GAT AGG GAA GAA TAT CAC TTC CAA ATG      288
Gln Lys Lys Leu Glu Arg Lys Asp Arg Glu Glu Tyr His Phe Gln Met
                 85                  90                  95

GCC GCT CCT AGT ATT GTG TCA AAA ATT ACT ATA GCT GGC GGA GAT CCT      336
Ala Ala Pro Ser Ile Val Ser Lys Ile Thr Ile Ala Gly Gly Asp Pro
                100                 105                 110

CCA TCA AAG TCT GAG CCA CAA GCA CCA AGA GGG ATC ATT CAT ACA ACT      384
Pro Ser Lys Ser Glu Pro Gln Ala Pro Arg Gly Ile Ile His Thr Thr
            115                 120                 125

CCA AGG ATG CGT AAA GTC AAG ACA CGC CCC ATA ATA AAG TTG ACA GAA      432
Pro Arg Met Arg Lys Val Lys Thr Arg Pro Ile Ile Lys Leu Thr Glu
        130                 135                 140

GGC CAG ATG AAT CAC CTC ATT AAG CAG ATA AAA CAG ATT ATG TCG GAG      480
Gly Gln Met Asn His Leu Ile Lys Gln Ile Lys Gln Ile Met Ser Glu
145                 150                 155                 160

AAA AGA GGG TCT GTC CAC TTA ATT AGT AAG AAA ACC ACT CAT GTT CAA      528
Lys Arg Gly Ser Val His Leu Ile Ser Lys Lys Thr Thr His Val Gln
                165                 170                 175

TAT AAG AAG ATA CTT GGT GCA TAC TCC GCA GCG GTT CGA ACT GCA CAT      576
Tyr Lys Lys Ile Leu Gly Ala Tyr Ser Ala Ala Val Arg Thr Ala His
                180                 185                 190

ATG ATG GGT TTG CGA CGG AGA GTG GAC TTC CGA TGT GAT ATG TGG ACA      624
Met Met Gly Leu Arg Arg Arg Val Asp Phe Arg Cys Asp Met Trp Thr
            195                 200                 205

GTT GGA CTT TTG CAA CGT CTC GCT CGG ACG GAC AAA TGG TCC AAT CAA      672
Val Gly Leu Leu Gln Arg Leu Ala Arg Thr Asp Lys Trp Ser Asn Gln
        210                 215                 220

GTC CGC ACT ATC AAC ATA CGA AGG GGT GAT AGT GGA GTC ATC TTG AAC      720
Val Arg Thr Ile Asn Ile Arg Arg Gly Asp Ser Gly Val Ile Leu Asn
225                 230                 235                 240

ACA AAA AGC CTC AAA GGC CAC TTT GGT AGA AGT TCA GGA GGC TTG TTC      768
Thr Lys Ser Leu Lys Gly His Phe Gly Arg Ser Ser Gly Gly Leu Phe
                245                 250                 255

ATA GTG CGT GGA TCA CAC GAA GGG AAA TTG TAT GAT GCA CGT TCT AGA      816
Ile Val Arg Gly Ser His Glu Gly Lys Leu Tyr Asp Ala Arg Ser Arg
                260                 265                 270

GTT ACT CAG AGT ATT TTA AAC TCA ATG ATC CAG TTT                      852
Val Thr Gln Ser Ile Leu Asn Ser Met Ile Gln Phe
            275                 280
```

(2) INFORMATION FOR SEQ ID NO:6:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Thr Tyr Met Ser Thr Ile Cys Phe Gly Ser Phe Glu Cys Lys
 1               5                  10                  15
Leu Pro Tyr Ser Pro Ala Ser Cys Glu His Ile Val Lys Glu Arg Glu
                20                  25                  30
Val Pro Ala Ser Val Asp Pro Phe Ala Asp Leu Glu Thr Gln Leu Ser
            35                  40                  45
Ala Arg Leu Leu Lys Gln Lys Tyr Ala Thr Val Arg Val Leu Lys Asn
        50                  55                  60
Gly Thr Phe Thr Tyr Arg Tyr Lys Thr Asp Ala Gln Ile Met Arg Ile
65                  70                  75                  80
Gln Lys Lys Leu Glu Arg Lys Asp Arg Glu Glu Tyr His Phe Gln Met
                85                  90                  95
Ala Ala Pro Ser Ile Val Ser Lys Ile Thr Ile Ala Gly Gly Asp Pro
            100                 105                 110
Pro Ser Lys Ser Glu Pro Gln Ala Pro Arg Gly Ile Ile His Thr Thr
        115                 120                 125
Pro Arg Met Arg Lys Val Lys Thr Arg Pro Ile Ile Lys Leu Thr Glu
130                 135                 140
Gly Gln Met Asn His Leu Ile Lys Gln Ile Lys Gln Ile Met Ser Glu
145                 150                 155                 160
Lys Arg Gly Ser Val His Leu Ile Ser Lys Lys Thr Thr His Val Gln
                165                 170                 175
Tyr Lys Lys Ile Leu Gly Ala Tyr Ser Ala Ala Val Arg Thr Ala His
            180                 185                 190
Met Met Gly Leu Arg Arg Arg Val Asp Phe Arg Cys Asp Met Trp Thr
        195                 200                 205
Val Gly Leu Leu Gln Arg Leu Ala Arg Thr Asp Lys Trp Ser Asn Gln
210                 215                 220
Val Arg Thr Ile Asn Ile Arg Arg Gly Asp Ser Gly Val Ile Leu Asn
225                 230                 235                 240
Thr Lys Ser Leu Lys Gly His Phe Gly Arg Ser Ser Gly Gly Leu Phe
                245                 250                 255
Ile Val Arg Gly Ser His Glu Gly Lys Leu Tyr Asp Ala Arg Ser Arg
            260                 265                 270
Val Thr Gln Ser Ile Leu Asn Ser Met Ile Gln Phe
        275                 280
```

(2) INFORMATION FOR SEQ ID NO:7:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..852

(xi) SEQUENCE DESCRIPTION: SEQ ID NO:7:

```
ATG GCA ACT TAC ATG TCA ACA ATC TGT TTC GGT TCA TTT GAA TGC AAG        48
Met Ala Thr Tyr Met Ser Thr Ile Cys Phe Gly Ser Phe Glu Cys Lys
1               5                   10                  15

CTA CCA TAC TCA CCC GCC TCT TGC GGG CAT ATT GTG AAG GAA CGA GAA        96
Leu Pro Tyr Ser Pro Ala Ser Cys Gly His Ile Val Lys Glu Arg Glu
                20                  25                  30

GTG CCA GCT TCC GTT GAT CCT TTC GCA GAT CTG GAA ACA CAA CTT AGT       144
Val Pro Ala Ser Val Asp Pro Phe Ala Asp Leu Glu Thr Gln Leu Ser
            35                  40                  45

GCA CGA TTG CGC AAG CAA GAA TAT GCT ACT GTT CGT GTG CTC AAG AAC       192
Ala Arg Leu Arg Lys Gln Glu Tyr Ala Thr Val Arg Val Leu Lys Asn
        50                  55                  60

GGT ACT TTT ACG TAC CGA TAC AAG ACT GAT GCC CAG ATA ATG CGC ATT       240
Gly Thr Phe Thr Tyr Arg Tyr Lys Thr Asp Ala Gln Ile Met Arg Ile
65                  70                  75                  80

CAG AAG AAA TTG GAG AGG AAA GAT AGG GAA GAA TAT CAC TTC CAA ATG       288
Gln Lys Lys Leu Glu Arg Lys Asp Arg Glu Glu Tyr His Phe Gln Met
                85                  90                  95

GCC GCT CCC AGT ATT GTG TCA AAA ATT ACT ATA GCT GGT GGA GAT CCT       336
Ala Ala Pro Ser Ile Val Ser Lys Ile Thr Ile Ala Gly Gly Asp Pro
                100                 105                 110

CCG TCA AAG TCT GAG CCA CAA GCA CCA AGA GGG ATA ATT CAT ACA ACT       384
Pro Ser Lys Ser Glu Pro Gln Ala Pro Arg Gly Ile Ile His Thr Thr
            115                 120                 125

CCA AAG GTG CGT AAA GTA AAG ACG CGC CCC ATA ATA AAG TTG ACA GAA       432
Pro Lys Val Arg Lys Val Lys Thr Arg Pro Ile Ile Lys Leu Thr Glu
        130                 135                 140

GGC CAG ATG AAT CAT CTC ATT AAG CAG GTA AAG CAG ATT ATG TCG GAG       480
Gly Gln Met Asn His Leu Ile Lys Gln Val Lys Gln Ile Met Ser Glu
145                 150                 155                 160

AAG AGA GGG TCT GTC CAT CTG ATT AGT AAG AAG ACC ACT CAT GTT CAA       528
Lys Arg Gly Ser Val His Leu Ile Ser Lys Lys Thr Thr His Val Gln
                165                 170                 175

TAT AAG GAG ATA CTT GGT GCA ACT CGT GCA GCG GTT CGA ACT GCA CAT       576
Tyr Lys Glu Ile Leu Gly Ala Thr Arg Ala Ala Val Arg Thr Ala His
                180                 185                 190

ATG ATG GGT TTG CGA CGG AGA GTG GAC TTC CGC TGT GAT ACG TGG ACA       624
Met Met Gly Leu Arg Arg Arg Val Asp Phe Arg Cys Asp Thr Trp Thr
            195                 200                 205

GTT GGA CTT TTG CAA CGT CTC GCT CGG ACG GAC AAA TGG TCC AAT CAA       672
Val Gly Leu Leu Gln Arg Leu Ala Arg Thr Asp Lys Trp Ser Asn Gln
        210                 215                 220

GTC CGC ACT ATC CAT GTA CGA AGG GGT GAT AGT GGG GTC ATC TTG AAC       720
Val Arg Thr Ile His Val Arg Arg Gly Asp Ser Gly Val Ile Leu Asn
225                 230                 235                 240

ACA AAA AGC CTC AAA GGC CAC TTT GGT AGA AGC TCA GGA GAT CTG TTC       768
Thr Lys Ser Leu Lys Gly His Phe Gly Arg Ser Ser Gly Asp Leu Phe
                245                 250                 255

ATA GTG CGT GGA TCA CAC GAA GGG AAA TTG TAC GAT GCA CGT TCT AGA       816
Ile Val Arg Gly Ser His Glu Gly Lys Leu Tyr Asp Ala Arg Ser Arg
                260                 265                 270

GTT ACT CAG AGT GTT TTG AAC TCA ATG ATC CAG TTT                       852
Val Thr Gln Ser Val Leu Asn Ser Met Ile Gln Phe
            275                 280
```

(2) INFORMATION FOR SEQ ID NO:8:

(i) SEQUENCE CHARACTERISTICS:
        (A) LENGTH: 284 amino acids

-continued

```
         (B) TYPE: amino acid
         (D) TOPOLOGY: linear (ii) MOLECULE TYPE: protein (xi) SEQUENCE DESCRIPTION: SEQ ID NO:8:

Met Ala Thr Tyr Met Ser Thr Ile Cys Phe Gly Ser Phe Glu Cys Lys
 1               5                  10                  15

Leu Pro Tyr Ser Pro Ala Ser Cys Gly His Ile Val Lys Glu Arg Glu
                20                  25                  30

Val Pro Ala Ser Val Asp Pro Phe Ala Asp Leu Glu Thr Gln Leu Ser
             35                  40                  45

Ala Arg Leu Arg Lys Gln Glu Tyr Ala Thr Val Arg Val Leu Lys Asn
         50                  55                  60

Gly Thr Phe Thr Tyr Arg Tyr Lys Thr Asp Ala Gln Ile Met Arg Ile
 65                  70                  75                  80

Gln Lys Lys Leu Glu Arg Lys Asp Arg Glu Glu Tyr His Phe Gln Met
                 85                  90                  95

Ala Ala Pro Ser Ile Val Ser Lys Ile Thr Ile Ala Gly Gly Asp Pro
                100                 105                 110

Pro Ser Lys Ser Glu Pro Gln Ala Pro Arg Gly Ile Ile His Thr Thr
            115                 120                 125

Pro Lys Val Arg Lys Val Lys Thr Arg Pro Ile Ile Lys Leu Thr Glu
            130                 135                 140

Gly Gln Met Asn His Leu Ile Lys Gln Val Lys Gln Ile Met Ser Glu
145                 150                 155                 160

Lys Arg Gly Ser Val His Leu Ile Ser Lys Lys Thr Thr His Val Gln
                165                 170                 175

Tyr Lys Glu Ile Leu Gly Ala Thr Arg Ala Ala Val Arg Thr Ala His
                180                 185                 190

Met Met Gly Leu Arg Arg Arg Val Asp Phe Arg Cys Asp Thr Trp Thr
            195                 200                 205

Val Gly Leu Leu Gln Arg Leu Ala Arg Thr Asp Lys Trp Ser Asn Gln
            210                 215                 220

Val Arg Thr Ile His Val Arg Arg Gly Asp Ser Gly Val Ile Leu Asn
225                 230                 235                 240

Thr Lys Ser Leu Lys Gly His Phe Gly Arg Ser Ser Gly Asp Leu Phe
                245                 250                 255

Ile Val Arg Gly Ser His Glu Gly Lys Leu Tyr Asp Ala Arg Ser Arg
            260                 265                 270

Val Thr Gln Ser Val Leu Asn Ser Met Ile Gln Phe
            275                 280
```